United States Patent [19]
Larson

[11] 4,144,592
[45] Mar. 20, 1979

[54] KNEE GUARD

[76] Inventor: Clinton F. Larson, 569 Sagewood Ave., Provo, Utah 84601

[21] Appl. No.: 881,643

[22] Filed: Feb. 24, 1978

[51] Int. Cl.² ............................................. A41D 13/06
[52] U.S. Cl. ...................................... 2/22; 2/24; 128/80 C
[58] Field of Search .................... 2/22, 24, 16, 62; 128/80 R, 80 C, 165, 80 B

[56] References Cited

U.S. PATENT DOCUMENTS

| | | | |
|---|---|---|---|
| 1,772,922 | 8/1930 | Volz | 2/22 |
| 2,144,641 | 1/1939 | Snyder | 2/22 |
| 2,195,024 | 3/1940 | Bullock | 2/22 X |
| 3,945,047 | 3/1976 | Jerrell | 2/24 |
| 4,024,584 | 5/1977 | Smith | 2/24 |
| 4,090,508 | 5/1978 | Gaylord | 128/80 C |

Primary Examiner—Louis Rimrodt
Attorney, Agent, or Firm—Clarence A. O'Brien; Harvey B. Jacobson

[57] ABSTRACT

A pair of elongated upstanding inner and outer stiff, but slightly flexible, members are provided for disposition along the thigh of the user with the inner member extending along and opposing the thigh and the outer member remote from the thigh. The members are at least slightly downwardly divergent and the outer member includes a lower end portion projecting below the lower end of the inner member. The knee guard defined by the inner and outer members may be secured to the user's thigh by tape bands encircling the thigh and overlying the outer surface of the inner member. The lower end portion of the outer member is to be horizontally registered with the associated knee and includes padding structure supported from the inner side thereof. A second form of the invention includes two pairs of inner and outer upstanding members connected together by means of horizontally disposed and rearwardly opening upper and lower generally U-shaped braces extending and secured between the upper ends of the pairs of members and the lower ends of the outer members. The inner surfaces of the U-shaped members are padded and a flexible panel extends along and is secured between the inner members throughout substantially their entire length and may be deflected forwardly to enclose an area slightly smaller than the area enclosed by the upper U-shaped brace.

15 Claims, 10 Drawing Figures

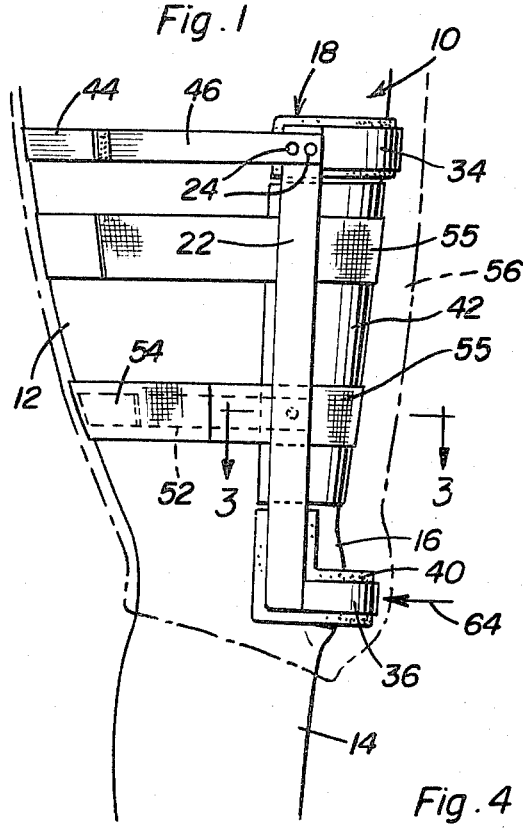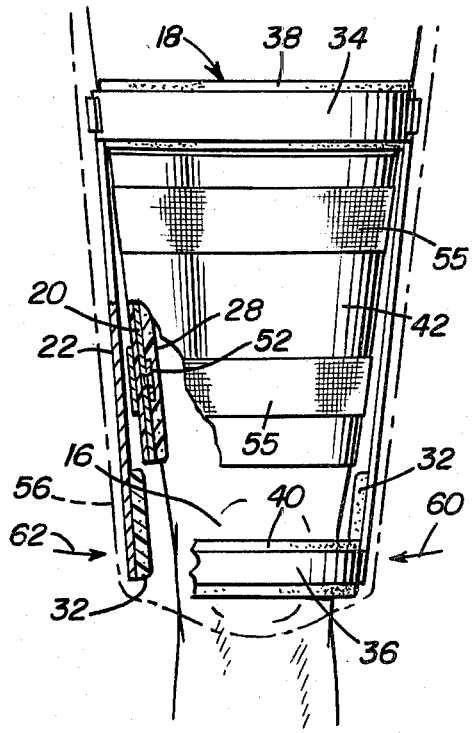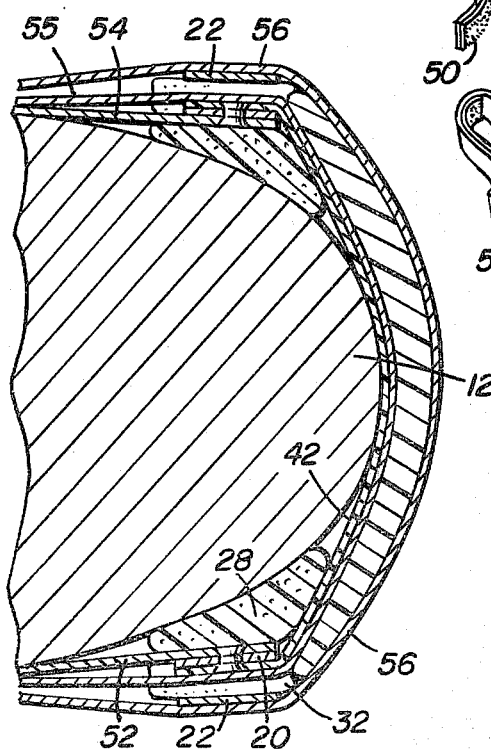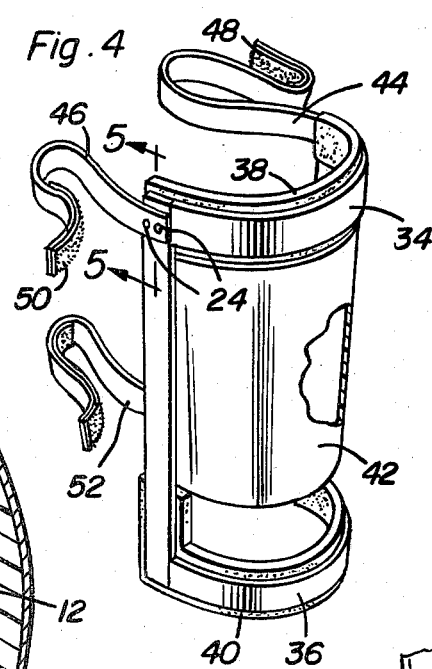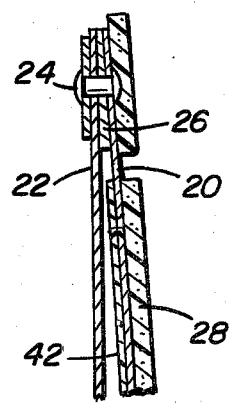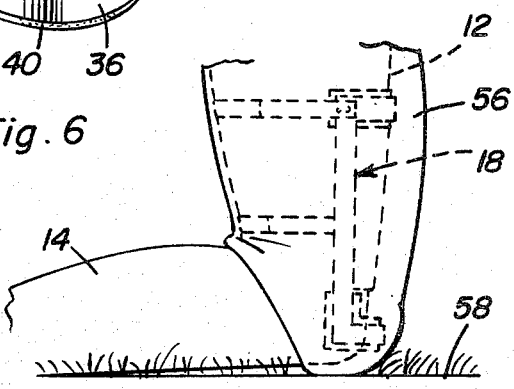

KNEE GUARD

BACKGROUND OF THE INVENTION

In many sports the participants are subject to serious and sometimes crippling knee injuries as a result of the knee being excessively laterally deflected relative to the associated hip and foot. Accordingly, a need exists for some form of knee guard which may be utilized to cushion and transmit at least a portion of lateral impact with a person's knee to the corresponding thigh. In this manner, the incidents of serious and sometimes crippling knee injuries may be greatly reduced.

Various forms of knee guards, protectors and braces, including some of the general structural and operational features of the instant invention are disclosed in U.S. Pat. Nos. 1,092,836, 1,131,816, 1,186,947, 1,622,211, 1,772,922 and 3,465,365.

BRIEF DESCRIPTION OF THE INVENTION

The knee guard of the instant invention is designed specifically to cushion lateral impact with the user's knee and to transmit at least a portion of the impact cushioned by the guard to the thigh above the associated knee.

The knee guard is illustrated and described hereinafter in two different forms, one form being designed to guard the associated knee against lateral impact from the outside thereof and the second form of guard being designed to protect the associated knee against lateral impact from both the inner and outer sides thereof as well as from the front side thereof.

The main object of this invention is to provide a knee guard which will be capable of cushioning and transmitting lateral impact forces directed toward the knee area of the user to the associated thigh.

Another object of this invention, in accordance with the immediately preceding object, is to provide a knee guard which will not interfere with the user assuming a kneeling position.

Yet another object of this invention is to provide a knee guard which will not interfere with articulation of the associated knee joint.

Another very important object of this invention is to provide a knee guard which may be readily worn beneath football trousers, and the like.

A further object of this invention is to provide a knee guard which may be readily supported from the user's thigh and which, independent of lateral forces being directed thereto, will be positioned in spaced relation relative to the associated knee joint.

Yet another object of this invention is to provide a knee guard which will also be operative to absorb rearward impact at the level of the associated knee.

A final object of this invention to be specifically enumerated herein is to provide a knee guard in accordance with the preceding objects and which will conform to conventional forms of manufacture, be of simple construction and easy to use, so as to provide a device that will be economically feasible, long lasting and relatively trouble-free in operation.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 1 is a side elevational view of a first form of guard constructed in accordance with the present invention operatively supported from the thigh of a user;

FIG. 2 is a front elevational view of the assemblage illustrated in FIG. 1 and with portions of the guard being broken away and illustrated in transverse vertical section;

FIG. 3 is an enlarged fragmentary, horizontal, sectional view taken substantially upon the plane indicated by the section line 3—3 of FIG. 1;

FIG. 4 is a perspective view of the assemblage illustrated in FIG. 1 and with a portion of the flexible impact absorbing panel thereof being broken away and illustrated in vertical section;

FIG. 5 is a fragmentary, enlarged, vertical, sectional view illustrating the interconnection between various components of one side of the upper portion of the guard;

FIG. 6 is a fragmentary, side, elevational view of a user of the guard with the associated leg in a kneeling position;

DETAILED DESCRIPTION OF THE INVENTION

Figure 7:
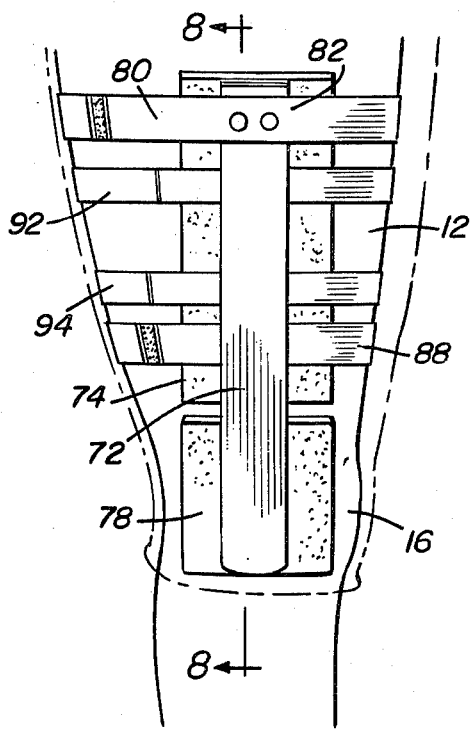
FIG. 7 is a side elevational view of a second form of guard constructed in accordance with the present invention and operatively mounted above an associated knee.
Figure 8:
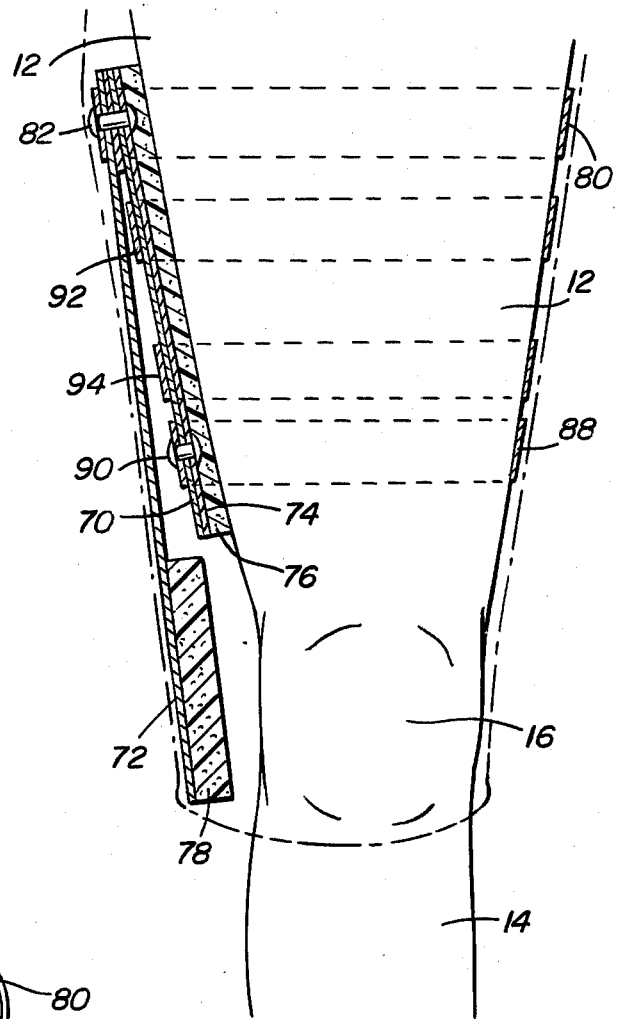
FIG. 8 is an enlarged, fragmentary, vertical, sectional view taken substantially upon the plane indicated by the section line 8—8 of FIG. 7.
Figure 9:
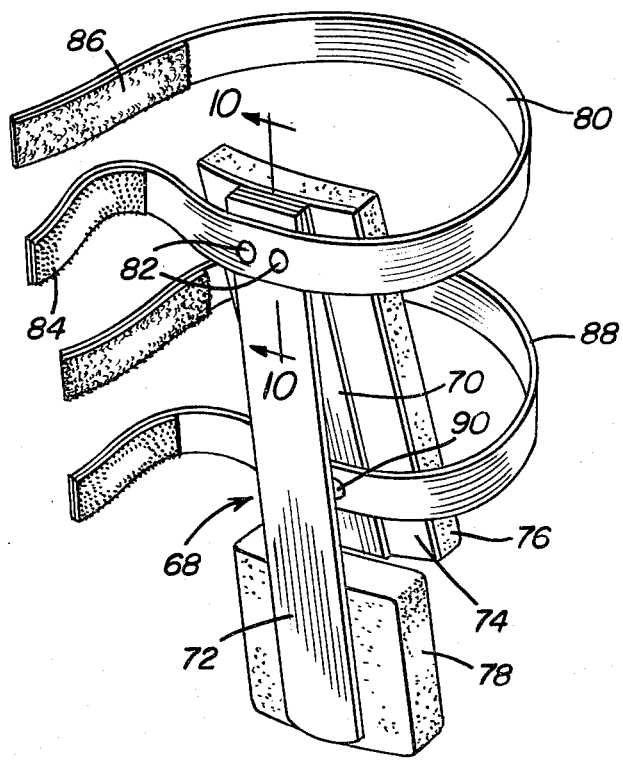
FIG. 9 is a perspective view of the second form of knee guard.

Referring now more specifically to the drawings, the numeral 10 generally designates a person's leg including an upper thigh portion 12, a lower leg portion 14 and a knee 16 supporting the leg 14 for articulation relative to the thigh 12.

A first form of knee guard is referred to in general by the reference numeral 18 and comprises two pairs of upstanding inner and outer members 20 and 22. The members 20 and 22 of each pair of members are slightly downwardly divergent and are secured together by means of suitable fasteners 24 with an upwardly tapering wedge 26 disposed between the opposing surfaces of the inner and outer members 20 and 22. The inner and outer members 20 and 22 each comprise stiff, but flexible, strap members and the inner side of each inner member 20 includes resilient padding 28 secured thereover. Further, the lower end of each outer member 22 projects below the lower end of the corresponding inner member 20 and has resilient padding 32 secured thereover. An upper rearwardly opening U-shaped member 34 extends between and is secured to the upper ends of the outer members 22 and a rearwardly opening lower generally U-shaped member 36 extends between and is secured to the lower ends of the outer members 22. The inner sides of the upper and lower U-shaped members 34 and 36 include resilient padding 38 and 40, respectively, secured thereover and a flexible panel 42 extends along and is secured to the inner members 20 in any convenient manner. The panel 42 is forwardly deflectable into a rearwardly opening generally U-shaped configuration and the plan area bounded by the forwardly deflected U-shaped panel 42 is slightly smaller than the plan area bounded by the upper U-shaped member. Further, the panel 42 is slightly smaller in width at its lower end whereby the panel 42 may conform to the downwardly tapering thigh 12 when the guard 18 is positioned relative to the thigh 12 in the manner illustrated in FIGS. 1 and 2 of the drawings.

The upper end portions of the outer members 22 include attaching straps 44 and 46 secured thereto and the straps include free ends equipped with complementary and releasably engageable Velcro strips 48 and 50. In addition, a similar pair of straps 52 and 54 are secured to the vertical midportions of the inner members 20. It will, of course, be appreciated that the straps 44 and 46 as well as the straps 52 and 54 may be utilized to secure the guard 18 to the thigh 12. In addition, bands 55 of suitable adhesive tape may be encircled about the thigh 12 and pass over the outer sides of the inner members 22.

From FIG. 6 of the drawings, it may be seen that the guard 18 may be worn beneath football trousers 56 and it will also be appreciated that the lower U-shaped member 36 is disposed in substantial horizontal registry with the knee 16 and, therefore, that the user may kneel upon the ground 58 in the manner illustrated in FIG. 6 without the guard 18 touching the ground or interfering with the user assuming a kneeling position.

In the event lateral impact is directed upon the lower portion of the guard 18 in either the direction 60 or the direction 62 indicated by arrows in FIG. 2, inward deflection of the lower end of the corresponding outer member will be transmitted to the associated inner member and thus to the thigh 12. Further, the padding 30 will absorb some of the impact of the lower end of the guard with the knee 16. Also, in the event rearward impact is directed upon the lower U-shaped member 36 in the direction of the arrow 64, the tendency of the lower ends of the outer members 22 to swing rearwardly will be resisted by the panel 42 and its engagement with the forward side of the thigh 12. In addition, the padding 40 carried by the lower U-shaped member 36 will also absorb some of the impact against the guard 18 in the direction of the arrow 64.

With attention now invited more specifically to FIGS. 7 through 10 of the drawings, there will be seen a modified form of knee guard referred to in general by the reference numeral 68. The knee guard 68 includes inner and outer members 70 and 72 corresponding to the inner and outer member 20 and 22 and the inner side of the inner member 70 may have a stiff backing panel 74 secured thereover from which the padding 76 corresponding to the padding 28 may be supported. In addition, the inner side of the lower end portion of the outer member 72 projecting below the lower end of the inner member 70 is equipped with padding 78 corresponding to the padding 32. Also, a single strap member 80 is secured, intermediate its opposite ends, to the upper end of the outer member 72 by means of fasteners 82 corresponding to the fasteners 24 and the opposite ends of the strap member 80 include Velcro strips 84 and 86 corresponding to the Velcro strips 48 and 50. In addition, a second strap member 88 of similar configuration is secured to the lower end portion of the inner member 70 by means of a fastener 90. Thus, it may be seen that the guard 68 may be applied to the outer surface of the thigh 12. In addition to the straps 80 and 88, bands 92 and 94 of tape may be secured about the thigh 12 and passed over the outer side of the inner member 70 at points spaced therealong.

Figure 10:
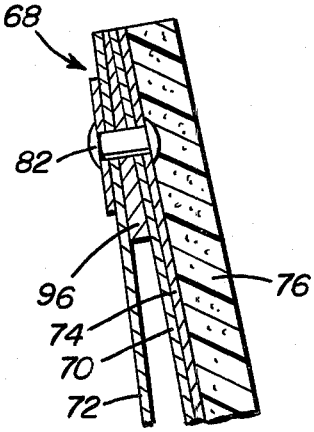
FIG. 10 is an enlarged, fragmentary, vertical, sectional view taken substantially upon the plane indicated by the section line 10—10 of FIG. 9.

From FIG. 10 of the drawings, it may be seen that an upwardly tapering wedge 96 corresponding to the wedges 26 is secured, by means of the fastener 82, between the upper ends of the inner and outer members 70 and 72.

In addition, it is to be understood that the inner members 20 of FIGS. 1-6 may have stiff backing panels corresponding to the backing panels 74 disposed between the inner members 20 and the corresponding padding 28. Further, the straps 52 and 54 may be attached to the vertical midportions of the inner members 20 in lieu of the vertical midportions of the outer members 22.

In operation, the guard 68 functions in substantially the same manner as the guard 18 for absorbing lateral impact to the knee 16 from the outer side thereof. However, the guard 68 does not offer protection against lateral impacts against the inner side of the knee 16 or rearward impacts against the knee 16.

The thigh 12 to which the guard 18 or the guard 68 is to be applied may be first wrapped. In this manner either guard may be mounted on the thigh not only by the corresponding straps, but also by bands 55 or 92, 94 of adhesive tape, or the like, secured about the thigh over the wrapping applied thereto. Also, the backing panel 74 is wider than the inner member 70 and the similar backing panels which may be provided on the inner members 20 may also be wider than the latter.

The members 20, 22 and 70, 72 may be constructed of spring steel or other suitable material of sufficient stiffness and yet resilient to the extent that horizontal impacts directed toward the associated knee will be effectively absorbed and/or transmitted to the associated thigh.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. A knee guard for protecting a person's knee against lateral deflection relative to his hip and foot, said guard including a pair of elongated upstanding inner and outer stiff, but slightly flexible members, means rigidly securing the upper ends of said members together, said members being at least slightly downwardly divergent and said outer member including a lower end portion projecting below the lower end of said inner member, said guard defining means for securing said guard to the thigh of a person with said inner member extending along and abutted against one side of said thigh and said outer member disposed on the side of said inner member remote from said thigh and said lower end portion horizontally registered with and spaced outwardly of said knee and said lower end of said inner portion spaced above said knee, the side of said outer member opposing said inner member including padding means supported therefrom spaced below said lower end of said inner member.

2. The combination of claim 1 wherein the inner side of said inner member includes a stiff backing strip secured thereover of a width greater than the width of said inner member.

3. The combination of claim 2 wherein the inner side of said backing strip includes a resilient pad secured thereover.

4. The combination of claim 1 wherein said means for securing said guard to the thigh of a person comprises said inner member over which bands of tape encircling said thigh may be secured.

5. The combination of claim 1 wherein said means for securing said guard to the thigh of a person comprises strap members carried by said inner member at points spaced therealong and adapted to be secured about said thigh.

6. The combination of claim 5 wherein said strap members have portions thereof spaced intermediate the opposite ends thereof secured to said inner member, at least the opposite ends of said strap members including complementary releasably engageable fastening means.

7. The combination of claim 6 wherein said fastening means comprise Velcro strip portions.

8. The combination of claim 1 wherein said guard includes a second pair of inner and outer elongated upstanding stiff, but slightly flexible members rigidly secured together at their upper ends, said second pair of members being downwardly divergent with the lower end portion of the outer member projecting below the lower end of said inner member and including padding means supported therefrom, said second pair of members being positionable along said thigh on the side remote from the first mentioned pair of members and with the outer member remote from said thigh, said means for securing said first mentioned pair of members from said thigh also including means for securing the inner member of said second pair of members to said thigh.

9. The combination of claim 1 wherein the inner side of the inner member of said second pair of members includes a stiff backing strip secured thereover of a width greater than the width of the second mentioned inner member.

10. The combination of claim 9 wherein the inner side of the last mentioned backing strip includes a resilient pad secured thereover.

11. The combination of claim 10 wherein said means for securing said guard to the thigh of a person includes said inner members over which bands of tape encircling said thigh may be secured.

12. A knee guard for protecting a person's knee against lateral deflection relative to his hip and foot, said guard including two pairs of elongated upstanding inner and outer stiff, but slightly flexible members, means rigidly securing the upper ends of each pair of said members together, each pair of members being slightly downwardly divergent and said outer members including lower end portions projecting downwardly below the lower ends of the corresponding inner members and having resilient pads overlying their inner surfaces, said pairs of members being spaced laterally apart with said inner and outer members disposed adjacent and remote from each other, an upper horizontal and generally U-shaped brace extending and secured between the upper ends of said pairs of members, a lower horizontal and generally U-shaped brace extending and secured between the lower ends of said outer members, said U-shaped members opening in the same horizontal direction and the inner surfaces of said U-shaped members including resilient padding secured thereover.

13. The combination of claim 12 wherein said guard includes a flexible panel extending and secured between said inner members, said panel being capable of being bowed to enclose an area slightly smaller than the area enclosed by said upper U-shaped member.

14. The combination of claim 12 wherein said means rigidly securing each pair of said members together includes an upwardly tapering wedge secured between each pair of inner and outer members.

15. The combination of claim 14 wherein said inner and outer members are at least substantially straight.

* * * * *